(12) United States Patent
Choi et al.

(10) Patent No.: US 12,114,938 B2
(45) Date of Patent: Oct. 15, 2024

(54) ROLLER MODULE FOR MEDICAL ROBOT, DRIVING DEVICE FOR MEDICAL ROBOT, AND MEDICAL ROBOT

(71) Applicant: LN ROBOTICS INC., Seoul (KR)

(72) Inventors: Jae Soon Choi, Seoul (KR); Young Hak Kim, Seoul (KR); Young Jin Moon, Seoul (KR)

(73) Assignee: LN ROBOTICS INC., Seoul (KR)

( * ) Notice: Subject to any disclaimer, the term of this patent is extended or adjusted under 35 U.S.C. 154(b) by 833 days.

(21) Appl. No.: 17/072,912

(22) Filed: Oct. 16, 2020

(65) Prior Publication Data

US 2021/0052339 A1 Feb. 25, 2021

Related U.S. Application Data

(63) Continuation of application No. PCT/KR2019/004770, filed on Apr. 19, 2019.

(30) Foreign Application Priority Data

Apr. 19, 2018 (KR) ........................ 10-2018-0045379

(51) Int. Cl.
*A61B 34/30* (2016.01)
*A61M 25/09* (2006.01)
(Continued)

(52) U.S. Cl.
CPC ............. *A61B 34/30* (2016.02); *A61M 25/09* (2013.01); *A61M 25/10* (2013.01); *F16H 1/222* (2013.01); *F16H 25/20* (2013.01)

(58) Field of Classification Search
CPC ... A61B 34/30; A61B 2034/301; A61B 34/35; A61B 34/20; A61B 2017/00398;
(Continued)

(56) References Cited

U.S. PATENT DOCUMENTS

2004/0254566 A1   12/2004   Plicchi et al.
2013/0035537 A1    2/2013   Wallace et al.
(Continued)

FOREIGN PATENT DOCUMENTS

CN   101138483 A   3/2008
CN   103157170 A   6/2013
(Continued)

OTHER PUBLICATIONS

International Search Report issued in PCT/KR2019/004770; mailed Jul. 25, 2019.

*Primary Examiner* — Mark W. Bockelman
(74) *Attorney, Agent, or Firm* — Studebaker & Brackett PC

(57) ABSTRACT

The present invention provides a medical robot which is hygienic and capable of precisely transferring a catheter, a driving device mounted on the medical robot, and a roller module mounted on the driving device. The roller module includes: a driving unit; and a roller unit rotated about the vertical axis by the driving unit, wherein the roller unit includes at least one roller and at least one shaft independently coupled to the at least one roller of the roller unit and rotated by the driving unit, wherein at least one groove is formed on the at least one roller of the roller unit and at least a part of the at least one shaft of the roller unit is disposed on the at least one groove.

10 Claims, 15 Drawing Sheets

(51) Int. Cl.
*A61M 25/10* (2013.01)
*F16H 1/22* (2006.01)
*F16H 25/20* (2006.01)

(58) Field of Classification Search
CPC .. A61M 25/09; A61M 25/10; A61M 25/0113; A61M 25/09041; F16H 1/222; F16H 25/20
See application file for complete search history.

(56) References Cited

U.S. PATENT DOCUMENTS

| | | | |
|---|---|---|---|
| 2015/0327938 A1 | 11/2015 | Bencteux et al. | |
| 2016/0008076 A1 | 1/2016 | Bencteux et al. | |
| 2020/0197111 A1* | 6/2020 | Kim ................ | A61M 25/09041 |

FOREIGN PATENT DOCUMENTS

| | | |
|---|---|---|
| CN | 105662586 A | 6/2016 |
| CN | 107847712 A | 3/2018 |
| JP | 2017-018619 A | 1/2017 |
| KR | 10-1133268 B1 | 4/2012 |
| KR | 10-2017-0035887 A | 3/2017 |
| WO | 2017-118818 A1 | 7/2017 |
| WO | 2017-158263 A1 | 9/2017 |

\* cited by examiner

ROLLER MODULE FOR MEDICAL ROBOT, DRIVING DEVICE FOR MEDICAL ROBOT, AND MEDICAL ROBOT

CROSS-REFERENCE TO RELATED APPLICATIONS

The present application is a continuation of International Patent Application No. PCT/KR2019/004770, filed on Apr. 19, 2019, which is based upon and claims the benefit of priority to Korean Patent Application No. 10-2018-0045379 filed on Apr. 19, 2018. The disclosures of the above-listed applications are hereby incorporated by reference herein in their entirety.

BACKGROUND

Embodiments of the inventive concept relate to a roller module for a medical robot, a driving device for a medical robot, and a medical robot.

Medical surgery may include a scheme in which a surgical tool (e.g., a balloon catheter, etc.) is inserted into a body to treat a disease related to blood vessels (e.g., cardiovascular coronary artery and peripheral artery interventions).

In this surgical process, X-rays based imaging should be performed to determine a location of the balloon catheter inserted into the body. Thus, there is a risk that a medical staff performing the surgery is exposed to a radiation of the X-ray.

In order to solve this problem, research on a medical robot that transports a catheter is being made. A medical staff may be protected from the X-ray radiation by controlling the medical robot through a radio signal in a space separate from a surgery site.

However, due to repeated use of a general medical robot, the robot may be contaminated with a patient's biomaterial. For this reason, the medical robot is cleaned to remove contaminants. However, when the robot is not completely cleaned, infection of the contaminants into a body may occur.

Further, the general medical robot may not accurately transfer a catheter based on a radio signal.

SUMMARY

Embodiments of the inventive concept provide a medical robot that may be hygienic, and precisely transport the catheter, a driving device mounted on the medical robot, and a roller module mounted on the driving device.

The purposes to be achieved by the inventive concept are not limited to the purposes mentioned above. Other purposes not mentioned will be clearly understood by those skilled in the art from following descriptions.

According to an exemplary embodiment, a roller module for a medical robot includes a driving unit, and a roller unit rotated by the driving unit while a rotation axis of the roller unit is a vertical direction, wherein the roller unit includes at least one roller, and at least one shaft independently coupled to the at least one roller of the roller unit and rotated by the driving unit, wherein the at least one roller of the roller unit has at least one hole or groove defined therein in which at least a portion of the at least one shaft of the roller unit is independently received.

The at least one hole or groove of the at least one roller of the roller unit may extend in the vertical direction, wherein a horizontal cross-section of the at least one hole or groove of the at least one roller of the roller unit may correspond to a horizontal cross-section of the at least one shaft of the roller unit.

Each of a shape of the horizontal cross-section of the at least one hole or groove of the at least one roller of the roller unit and a shape of the horizontal cross-section of the at least one shaft of the roller unit may have a shape extending in a first direction and a second direction in a horizontal plane and intersecting with each other at a center point in a right manner.

The driving unit may include a first driving motor, wherein a rotation axis of the first driving motor of the driving unit and a rotation axis of the at least one shaft of the roller unit may be perpendicular to each other.

The driving unit further may include a first driving shaft, wherein a spur gear of the first driving motor of the driving unit may mesh with a spur gear of the first driving shaft of the driving unit, wherein at least one bevel gear of the at least one shaft of the roller unit may independently mesh with at least one bevel gear of the first driving shaft of the driving unit.

The roller unit may move in the vertical direction by the driving unit.

The roller unit further may include a screw, a nut meshing with the screw of the roller unit, and a casing disposed on the nut of the roller unit, wherein the screw of the roller unit may be rotated by the driving unit, wherein the nut of the roller unit may move in the vertical direction via rotation of the screw of the roller unit, wherein the casing of the roller unit may move in the vertical direction by the nut of the roller unit.

The casing of the roller unit may include a pivotable hook, wherein the nut of the roller unit may include a bar locked and unlocked by the hook of the casing.

The driving unit may include a second driving motor, wherein a rotation axis of the second driving motor of the driving unit and a rotation axis of the screw of the roller unit may be perpendicular to each other.

The driving unit further may include a second driving shaft, wherein a spur gear of the second driving motor of the driving unit may mesh with a spur gear of the second driving shaft of the driving unit, wherein a bevel gear of the screw of the roller unit may mesh with a bevel gear of the second driving shaft of the driving unit.

According to an exemplary embodiment, a driving device for a medical robot includes a base module, and a first roller module and a second roller module, wherein a spacing between the first roller module and the second roller module is controlled by the base module, wherein at least one of the first roller module or the second roller module includes a driving unit, and a roller unit rotated by the driving unit while a rotation axis of the roller unit is a vertical direction, wherein the roller unit includes at least one roller, and at least one shaft independently coupled to the at least one roller of the roller unit and rotated by the driving unit, wherein the at least one roller of the roller unit has at least one hole or groove defined therein in which at least a portion of the at least one shaft of the roller unit may be independently received.

At least one of a guide catheter, a guide wire, and a balloon catheter may be disposed and clamped between the first roller module and the second roller module, and then may be transferred via rotation of a roller unit of the first roller module and a roller unit of the second roller module, wherein rotation axes of the roller unit of the first roller module and the roller unit of the second roller module may be parallel to each other, and rotation directions of the roller unit of the first roller module and the roller unit of the second roller module may be opposite to each other.

Each of the roller unit of the first roller module and the roller unit of the second roller module may be removable in a cartridge form.

The base module may include a base body, a first nut disposed on the base body of the base module and coupled to the first roller module, a second nut disposed on the base body of the base module and coupled to the second roller module, a screw meshing with the first nut of the base module and the second nut of the base module, and a first driving motor to rotate the screw of the base module, wherein forward or reverse rotation of the screw of the base module may allow the first nut of the base module and the second nut of the base module to move such that a spacing between the first roller module and the second roller module varies.

The driving unit of the first roller module may include a first casing, a first driving motor and a first driving shaft disposed inside the first casing of the driving unit of the first roller module to rotate the roller unit of the first roller module, and a second driving motor and a second driving shaft disposed inside the first casing of the driving unit of the first roller module to move the roller unit of the first roller module in the vertical direction, wherein the driving unit of the second roller module may include a second casing, a first driving motor and a first driving shaft disposed inside the second casing of the driving unit of the second roller module to rotate the roller unit of the second roller module, and a second driving motor and a second driving shaft disposed inside the second casing of the driving unit of the second roller module to move the roller unit of the second roller module in the vertical direction, wherein the first casing of the driving unit of the first roller module may be supported by the first nut of the base module, wherein the second casing of the driving unit of the second roller module may be supported by the second nut of the base module.

A gearbox may be disposed between the first driving motor of the base module and the screw of the base module.

The base module further may include a second driving motor, and a belt connecting a spur gear of the first driving motor of the base module and a spur gear of the second driving motor of the base module to each other, wherein rotation of the first driving motor of the base module and rotation of the second driving motor of the base module may be associated with each other via the belt of the base module.

A spiral rotation direction in which the screw of the base module and the first nut of the base module mesh with each other, and a spiral rotation direction in which the screw of the base module and the second nut of the base module mesh with each other may be opposite to each other.

According to an exemplary embodiment, a medical robot includes a first driving device, a second driving device, and a third driving device to transport a guide catheter, a guide wire, and a balloon catheter, respectively, wherein at least one of the first driving device, the second driving device, or the third driving device includes a base module, and a first roller module and a second roller module, wherein a spacing between the first roller module and the second roller module is controlled by the base module, wherein at least one of the first roller module or the second roller module includes a driving unit, and a roller unit rotated by the driving unit while a rotation axis of the roller unit is a vertical direction, wherein the roller unit includes at least one roller, and at least one shaft independently coupled to the at least one roller of the roller unit and rotated by the driving unit, wherein the at least one roller of the roller unit has at least one hole or groove defined therein in which at least a portion of the at least one shaft of the roller unit is independently received, wherein at least one of the guide catheter, the guide wire, and the balloon catheter is disposed and clamped between the first roller module and the second roller module, and then is transferred via rotation of a roller unit of the first roller module and a roller unit of the second roller module, wherein rotation axes of the roller unit of the first roller module and the roller unit of the second roller module are parallel to each other, and rotation directions of the roller unit of the first roller module and the roller unit of the second roller module are opposite to each other.

The guide catheter may be clamped to the first driving device, the guide wire may be clamped to the second driving device, the balloon catheter may be clamped to the third driving device, wherein the guide catheter may accommodate the guide wire and the balloon catheter therein.

A travel direction of the first driving device and a travel direction of the second driving device may be in the same straight line, while the travel direction of the first driving device and a travel direction of the third driving device may intersect with each other.

The medical robot may further include a first connector disposed between the first driving device and the second driving device to support the guide catheter, the guide wire, and the balloon catheter at the same time, wherein the first connector may move in the travel directions of the first driving device and the second driving device.

The first connector may include a first connector body fixing the guide catheter, the guide wire and the balloon catheter, and a first connector support extending downward from the first connector body.

A travel direction of the first driving device and a travel direction of the second driving device may intersect with each other, wherein the travel direction of the first driving device and a travel direction of the third driving device may intersect with each other, wherein the travel direction of the second driving device and the travel direction of the third driving device may intersect with each other.

The travel direction of the first driving device, the travel direction of the second driving device, and the travel direction of the third driving device may intersect with each other at a single intersection.

The medical robot may further include a second connector having a single intersection at which the travel directions of the first driving device, the second driving device, and the third driving device intersect with each other, wherein the second connector may include a first receiving portion accommodating the guide catheter, a second receiving portion accommodating the guide wire, and a third receiving portion accommodating the balloon catheter, wherein the first receiving portion of the second connector may be connected to the second receiving portion of the second connector and the third receiving portion of the second connector.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
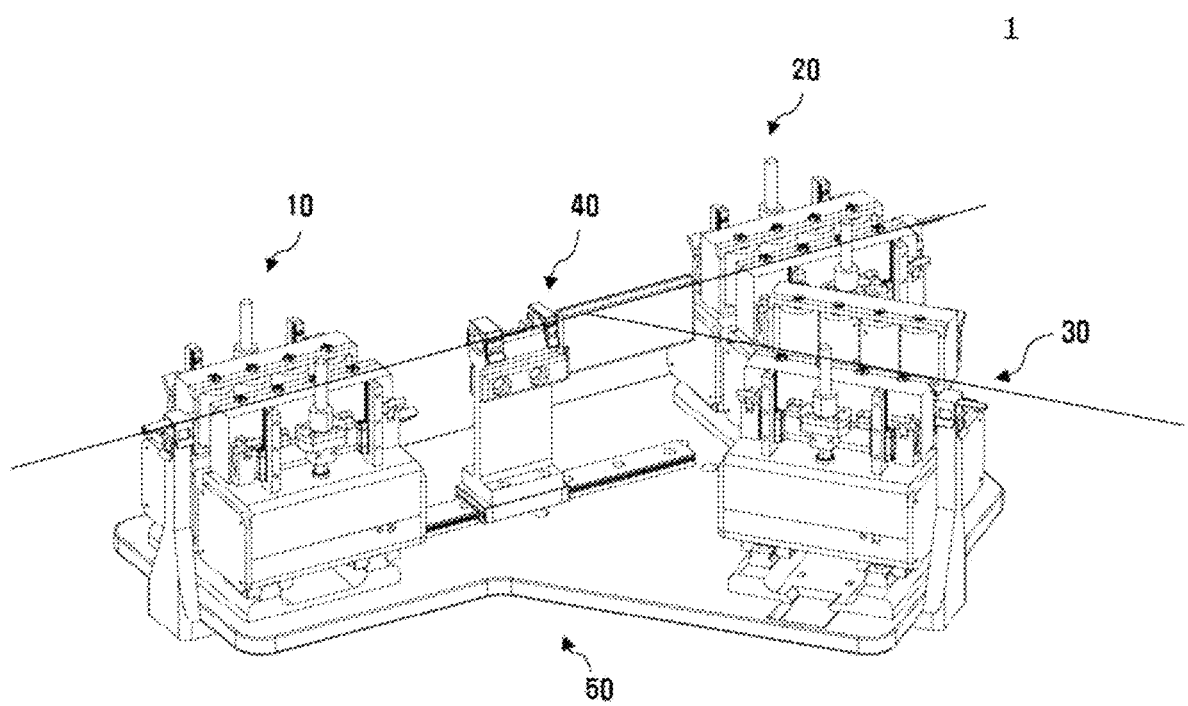
FIG. 1 is a perspective view showing a medical robot of the inventive concept.

Advantages and features of the inventive concept, and a method of achieving them will become apparent with reference to embodiments described below in detail together with the accompanying drawings. However, the inventive concept is not limited to the embodiments disclosed below, but may be implemented in various different forms. The present embodiments are provided to merely complete the disclosure of the inventive concept, and to merely fully inform those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or greater other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, when the device in the FIG. is turned over, elements described as "below" or "beneath" or "under" other elements or features would then be oriented "above" the other elements or features. Thus, the example terms "below" and "under" may encompass both an orientation of above and below. The device may be otherwise oriented for example, rotated 90 degrees or at other orientations, and the spatially relative descriptors used herein should be interpreted accordingly.

Hereinafter, a term "vertical direction" may mean an up-down direction in a drawing. Furthermore, the "vertical direction" may be parallel to a rotation axis of a "rolling operation mode". That is, a rotation axis of a roller unit may be parallel to the "vertical direction".

Hereinafter, a medical robot 1 of the inventive concept will be described with reference to the drawings. The medical robot 1 of the inventive concept may transport a guide catheter 61, a guide wire 62 and a balloon catheter 63 for surgery. In this case, the surgery may be interventional surgery of coronary arteries and peripheral arteries of a cardiovascular system. In the interventional surgery, the balloon catheter 63 is inserted into a cardiac blood vessel, such that a blocked blood vessel is artificially widened to treat a heart disease.

The guide catheter 61 may be a hollow tube accommodating therein the guide wire 62 and the balloon catheter 63. The guide wire 62 has a length, and supports and guides the balloon catheter 63.

As shown in FIG. 1, the medical robot 1 of the inventive concept may include a first driving device 10, a second driving device 20, a third driving device 30, a first connector 40, and a support plate 50.

The first driving device 10, the second driving device 20, and the third driving device 30 may transport the guide catheter 61, the guide wire 62, and the balloon catheter 63. In this case, the guide catheter 61 may be clamped to the first driving device 10, the guide wire 62 may be clamped to the second driving device 20, and the balloon catheter 63 may be clamped to the third driving device 30.

In order to transport the guide catheter 61, the guide wire 62 and the balloon catheter 63, the first driving device 10, the second driving device 20 and the third driving device 30 may perform "rolling operation mode", "clamping operation mode" and "vertical operation mode.

Figure 2:
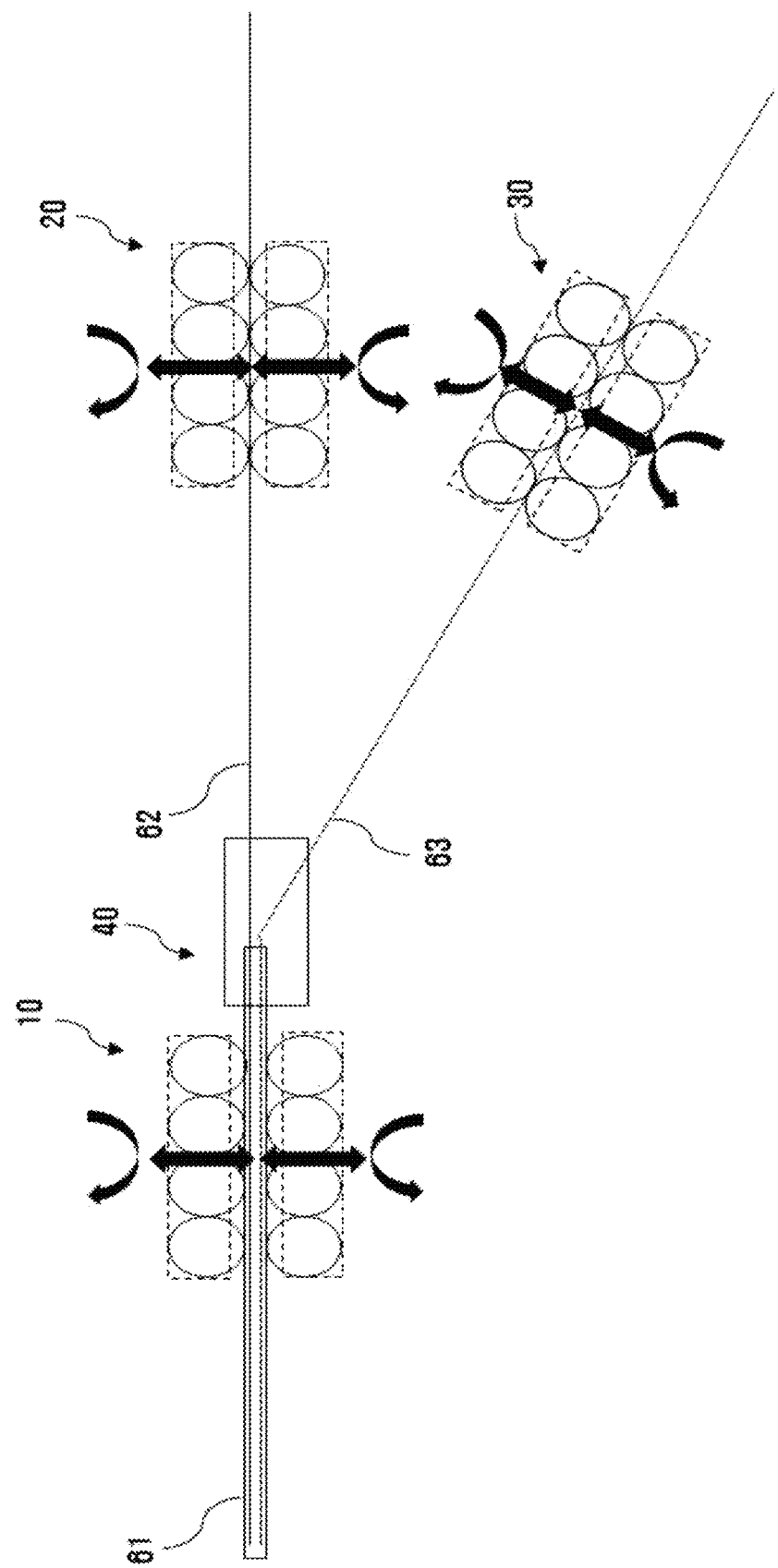
FIG. 2 is a conceptual diagram showing a rolling operation mode and a clamping operation mode of a medical robot equipped with a first connector of the inventive concept.
Figure 3:
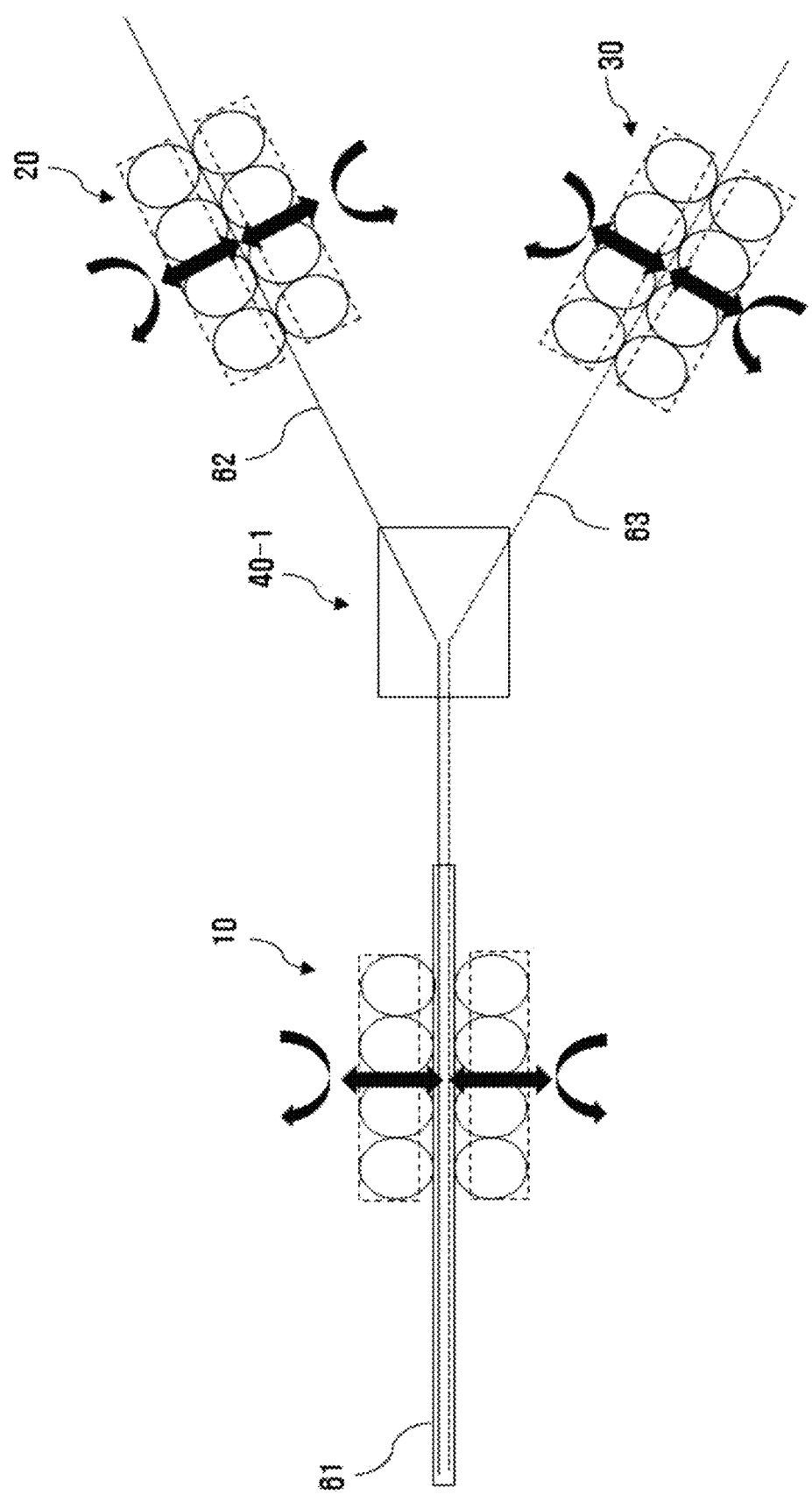
FIG. 3 is a conceptual diagram showing a rolling operation mode and a clamping operation mode of a medical robot equipped with a second connector of the inventive concept.
Figure 4A:
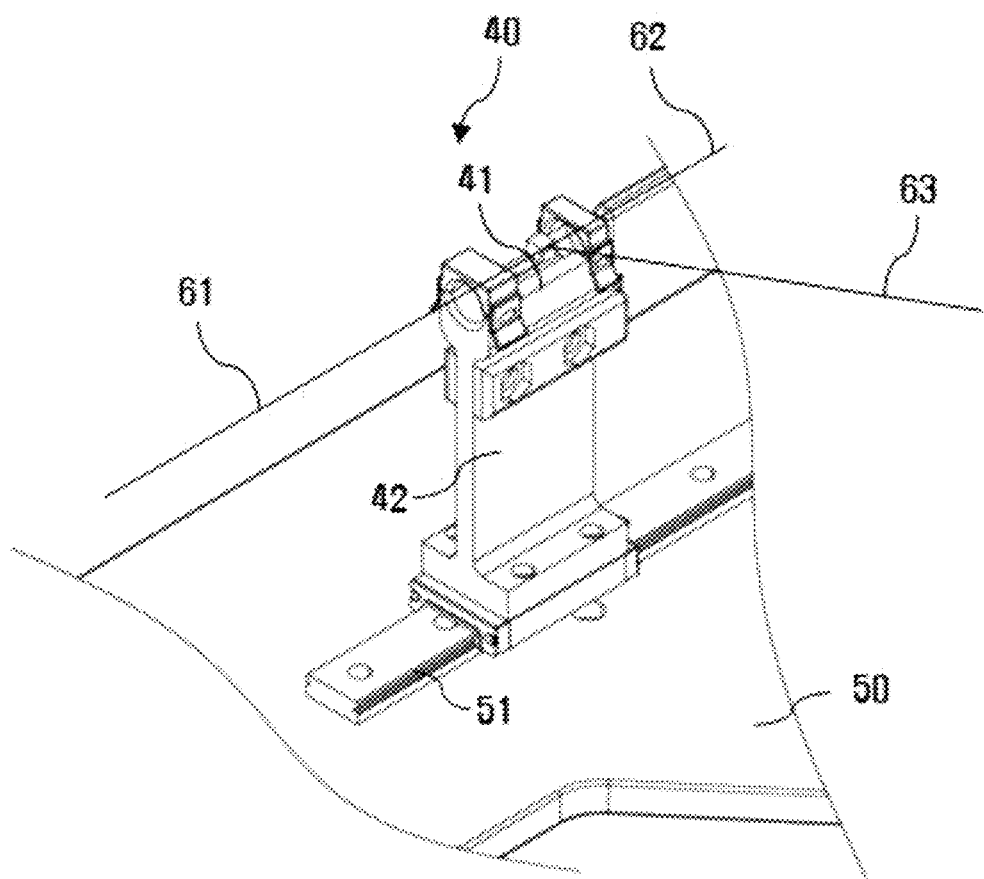
FIGS. 4A and 4B are perspective views showing a first connector and a second connector of a medical robot of the inventive concept.
Figure 4B:
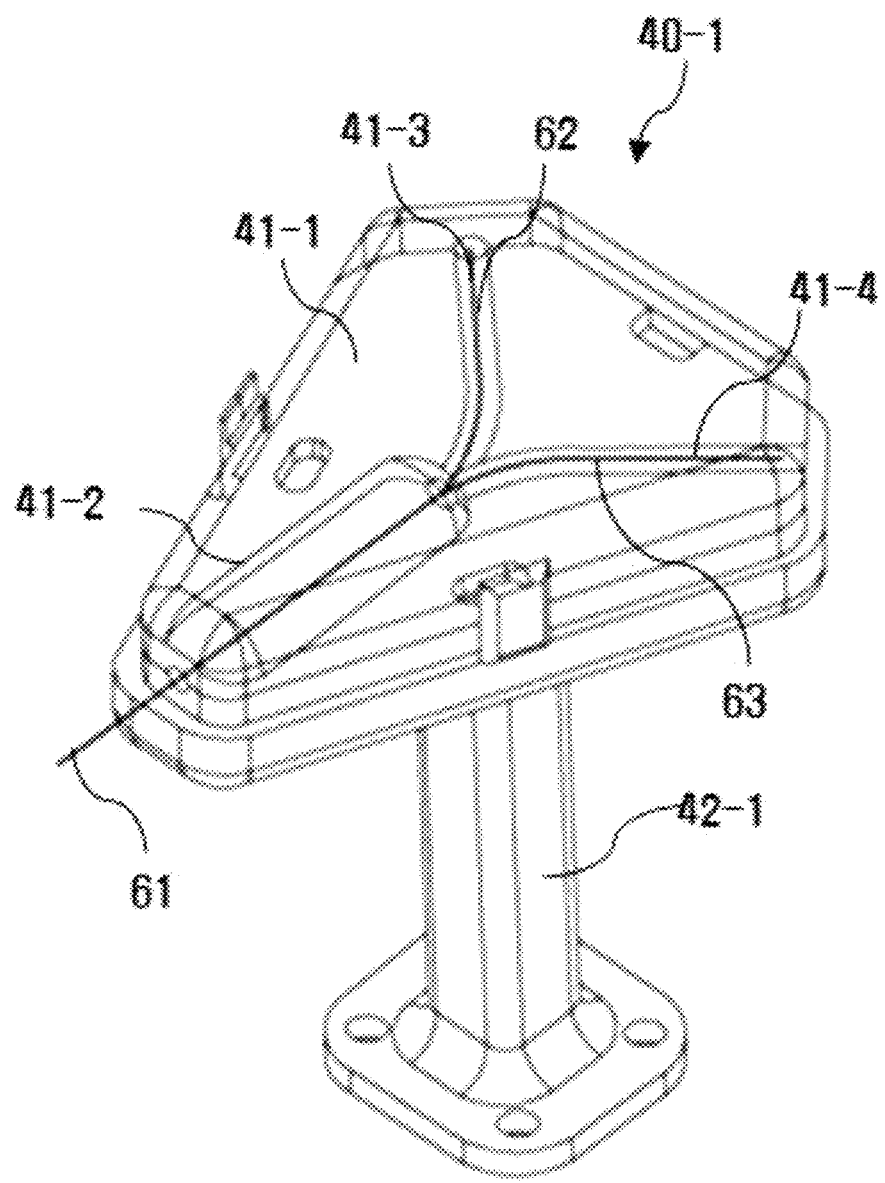

Referring to FIG. 2 and FIG. 3, in the "rolling operation mode", a roller unit of each of the first driving device 10, the second driving device 20 and the third driving device 30 rotates, such that the guide catheter 61, the guide wire 62 and the balloon catheter 63 travel in a longitudinal direction.

Further, referring to FIG. 2 and FIG. 3, in the "clamping operation mode", mutually opposed roller units of each of the first driving device 10, the second driving device 20, and the third driving device 30 become closer to or farther away from each other, such that a clamping degree of each of the guide catheter 61, the guide wire 62 and the balloon catheter 63 is controlled.

Figure 5A:
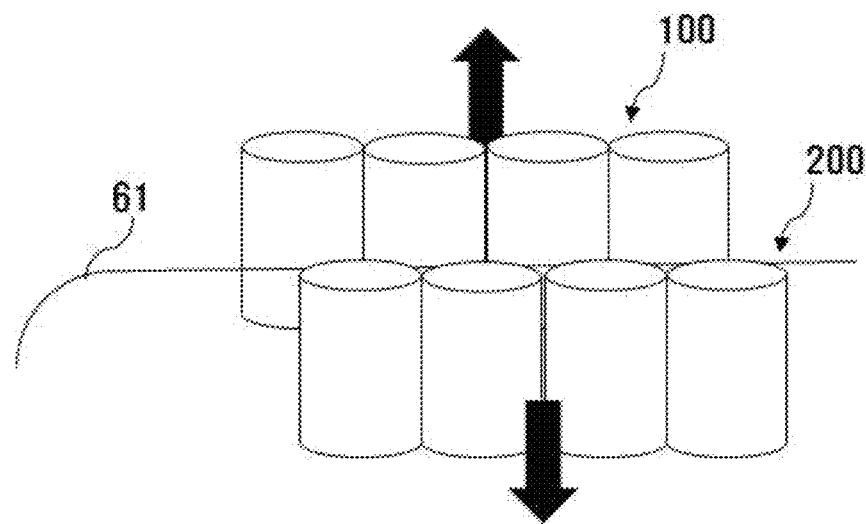
FIGS. 5A and 5B are conceptual diagrams showing a vertical operation mode of a first driving device of a medical robot of the inventive concept.
Figure 5B:
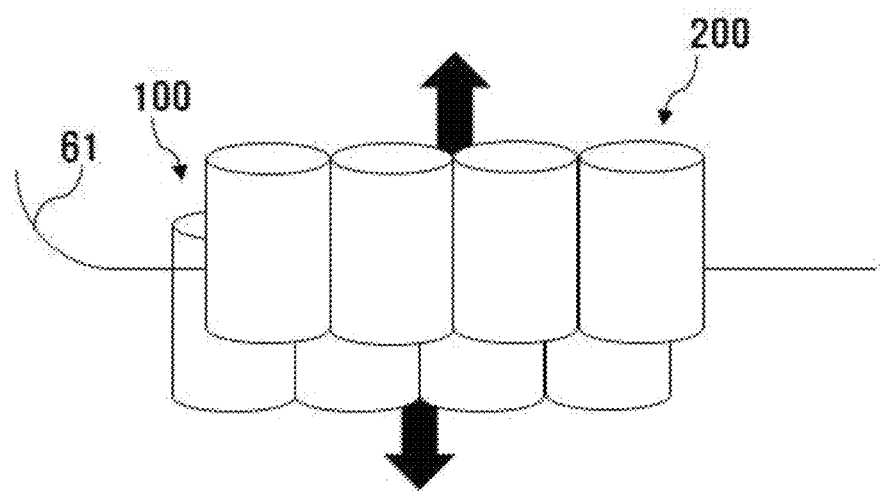
Figure 6:
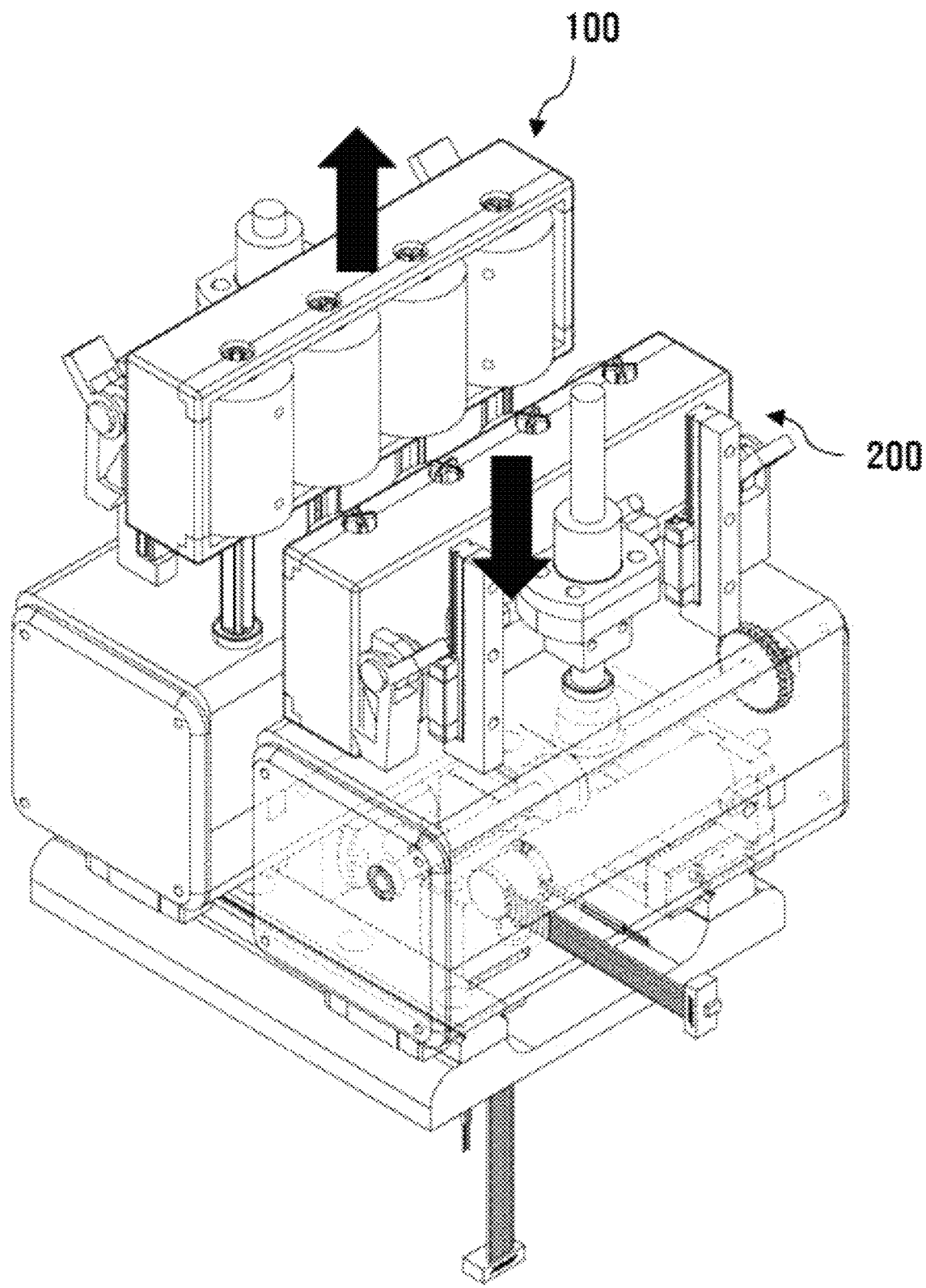
FIG. 6 is a perspective view showing a vertical operation mode of a first driving device of a medical robot of the inventive concept.
Figure 7:
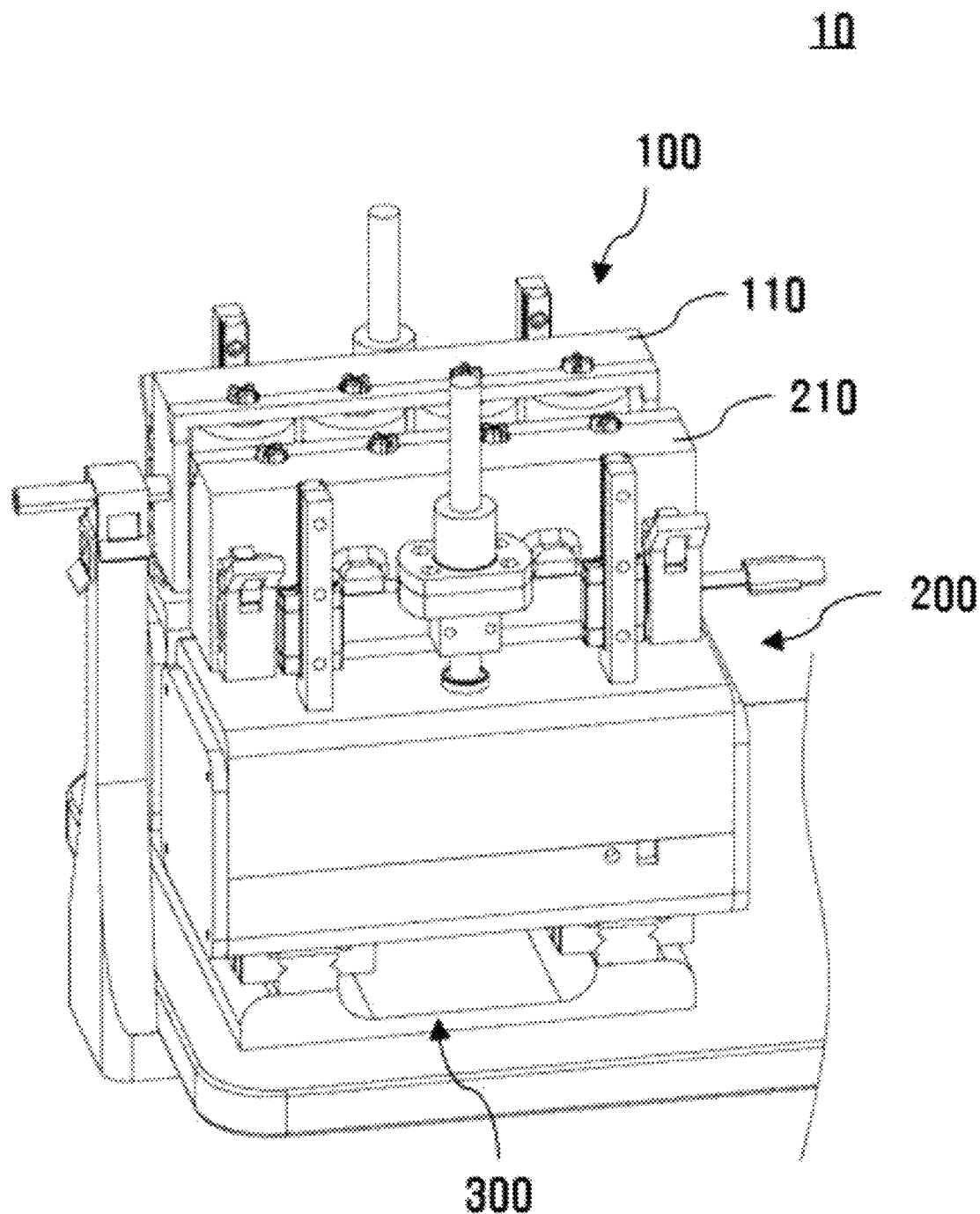
FIG. 7 is a perspective view showing a first driving device of the inventive concept.

In one example, referring to FIGS. 5A and 5B, and FIG. 6, in the "vertical operation mode", rollers of each of the first driving device 10, the second driving device 20 and the third driving device 30 move in the vertical direction to rotate each of the guide catheter 61, the guide wire 62 and the balloon catheter 63 having an curved end, thereby to determine a travel direction of each of the guide catheter 61, the guide wire 62 and the balloon catheter 63.

The medical robot 1 of the inventive concept is characterized by precisely transferring the guide catheter 61, the guide wire 62 and the balloon catheter 63 using the above-described three operations.

Further, in the medical robot 1 of the inventive concept, the roller unit is manufactured in a form of a cartridge, and may be replaced, so that surgery may be performed hygienically.

In one example, the first driving device 10, the second driving device 20, and the third driving device 30 of the medical robot 1 of the inventive concept may have two arrangements.

First, referring to FIG. 2 to describe a first arrangement, a travel direction of the first driving device 10 and a travel direction of the second driving device 20 may be in the same straight line, while the travel direction of the first driving device 10 and a travel direction of the third driving device 30 may intersect with each other.

In this case, the first connector 40 may be used. The first connector 40 is disposed between the first driving device 10 and the second driving device 20 to support the guide catheter 61, the guide wire 62 and the balloon catheter 63 at the same time.

Furthermore, the first connector 40 may move in the travel direction of the first driving device 10 and the second driving device 20 in order to stably support the guide catheter 61, the guide wire 62 and the balloon catheter 63.

To this end, the first connector 40 may include a first connector body 41 fixing the guide catheter 61, the guide wire 62 and the balloon catheter 63, and a first connector support 42 extending downward from the first connector body 41.

Furthermore, a support plate rail 51 for guiding movement of the first connector support 42 of the first connector 40 may be formed on the support plate 50.

Hereinafter, referring to FIG. 3 to describe a second arrangement, the travel direction of the first driving device 10 and the travel direction of the second driving device 20 may intersect with each other, while the travel direction of the first driving device 10 and the travel direction of the third driving device 30 may intersect with each other, while the travel direction of the second driving device 20 and the travel direction of the third driving device 30 may intersect with each other. Furthermore, the travel direction of the first driving device 10, the travel direction of the second driving device 20, and the travel direction of the third driving device 30 may intersect with each other at a single intersection.

In this case, a second connector 40-1 may be used. The second connector 40-1 is a "Y-shaped connector" in which the single intersection between the travel directions of the first driving device 10 and the second driving device 20 and the third driving device 30 is defined.

The second connector 40-1 includes a second connector body 41-1 and a second connector support 42-1 extending downward from the second connector body 41-1 to support the second connector body 41-1.

In one example, the second connector body 41-1 may include a first receiving portion 41-2 for accommodating the guide catheter 61, a second receiving portion 41-3 for accommodating the guide wire 62, and a third receiving portion 41-4 for accommodating the balloon catheter 63. In this case, the first receiving portion 41-2 of the second connector 40-1 may be connected with both of the second receiving portion 41-3 of the second connector 40-1 and the third receiving portion 41-4 of the second connector 40-1.

Hereinafter, the first driving device 10 of the medical robot 1 of the inventive concept will be described with reference to the drawings. In one example, a configuration of the first driving device 10 may be equally applied to the second driving device 20 and the third driving device 30. That is, the first driving device 10, the second driving device 20, and the third driving device 30 may have substantially the same technical configuration.

The first driving device 10 may include a first roller module 100, a second roller module 200, and a base module 300.

A roller unit 110 of the first roller module 100 and a roller unit 210 of the second roller module 200 may face away each other. The roller unit 110 of the first roller module 100 and the roller unit 210 of the second roller module 200 respectively have rotation axes parallel to each other, and rotation directions thereof may be opposite to each other.

The "rolling operation mode" of the first driving device 10 may be performed by rotating the roller unit 110 of the first roller module 100 and the roller unit 210 of the second roller module 200 in opposite directions to each other.

The "clamping operation mode" of the first driving device 10 may be achieved by bringing the roller unit 110 of the first roller module 100 and the second roller unit 210 of the second roller module 200 closer to each other or moving away from each other.

The "vertical operation mode" of the first driving device 10 may be achieved by moving the roller unit 110 of the first roller module 100 and the roller unit 210 of the second roller module 200 in opposite directions to each other in the vertical direction.

Further, each of the roller unit 110 of the first roller module 100 and the roller unit 210 of the second roller module 200 may be replaced in a form of a cartridge.

First, the first roller module 100 will be described. In one example, a configuration of the first roller module 100 may be equally applied to the second roller module 200. In other words, the first roller module 100 and the second roller module 200 may have substantially the same technical configuration.

Figure 8:
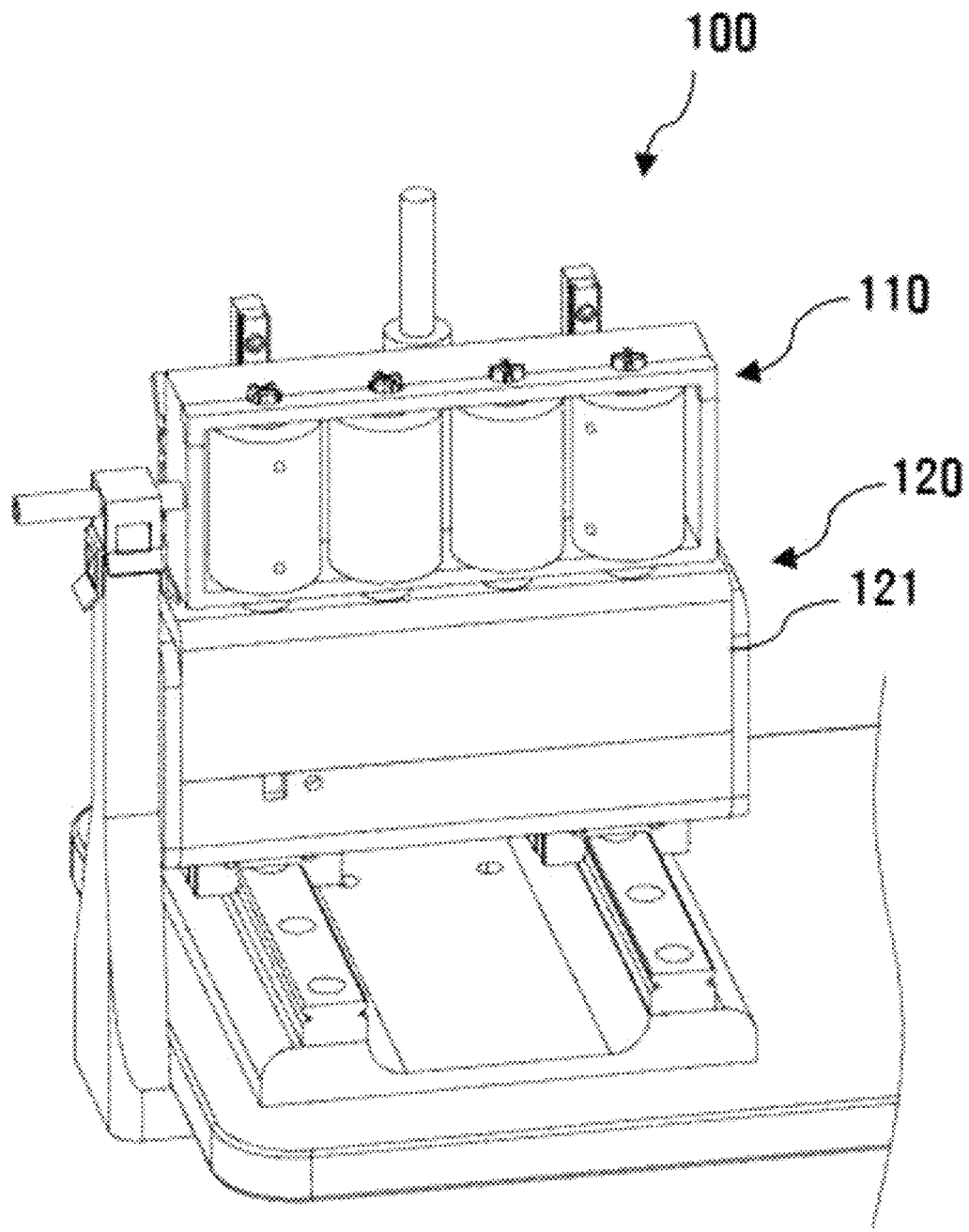
FIG. 8 is a perspective view showing a first roller module of the inventive concept.

As shown in FIG. 8, the first roller module 100 may include the roller unit 110 and a driving unit 120.

The roller unit 110 may include at least one roller 111 and at least one shaft 114 that may be independently coupled with the at least one roller 111 of the roller unit 110 respectively, and may be rotated by the driving unit 120.

Figure 9:
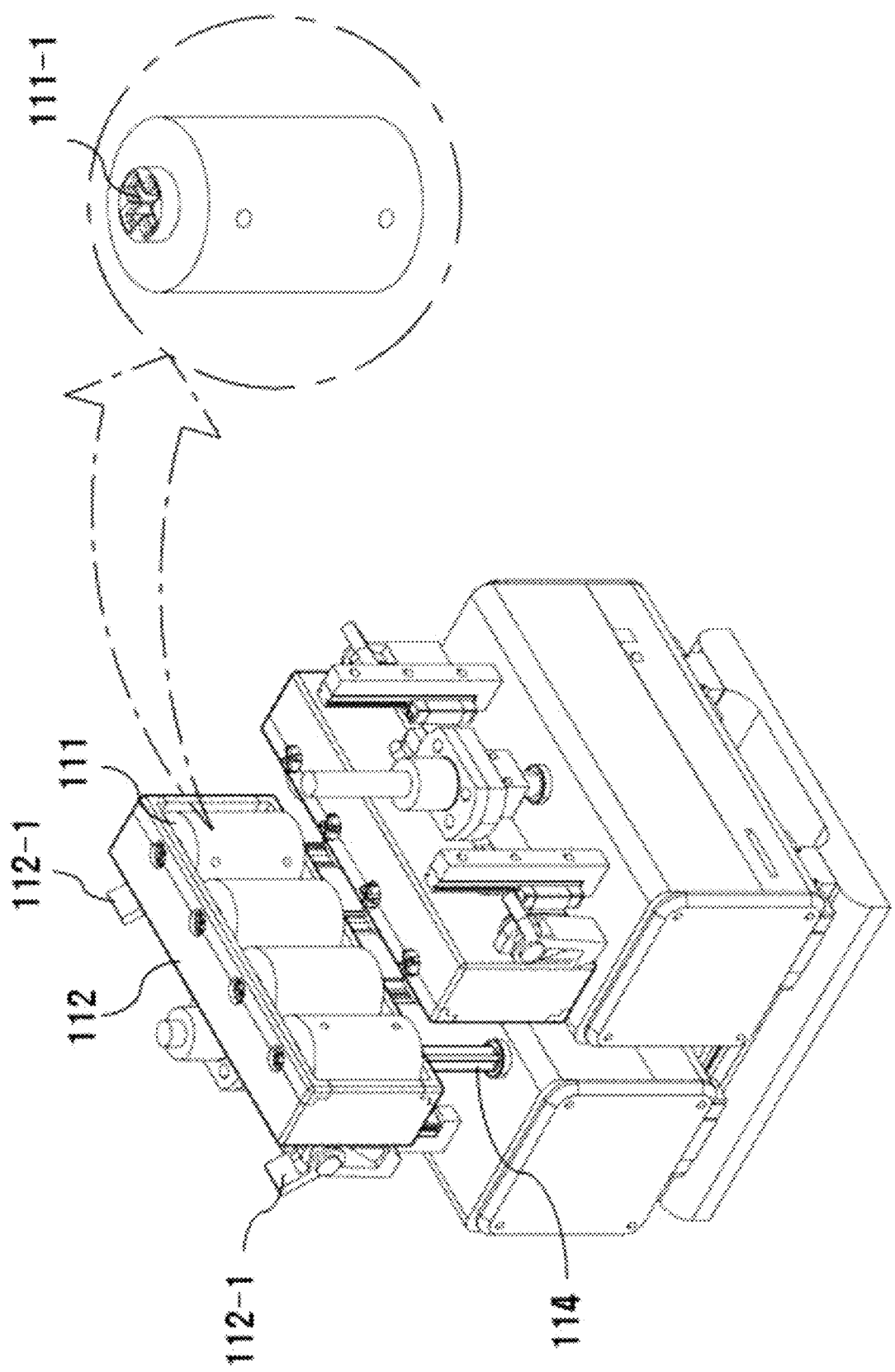
FIG. 9 is a perspective view showing that a groove or hole is formed in a roller of a first roller module of the inventive concept.

As shown in FIG. 9, the at least one roller 111 of the roller unit 110 has at least one hole or groove 111-1 defined therein into which at least a portion of the at least one shaft 114 of the roller unit 110 is independently received.

Figure 13:
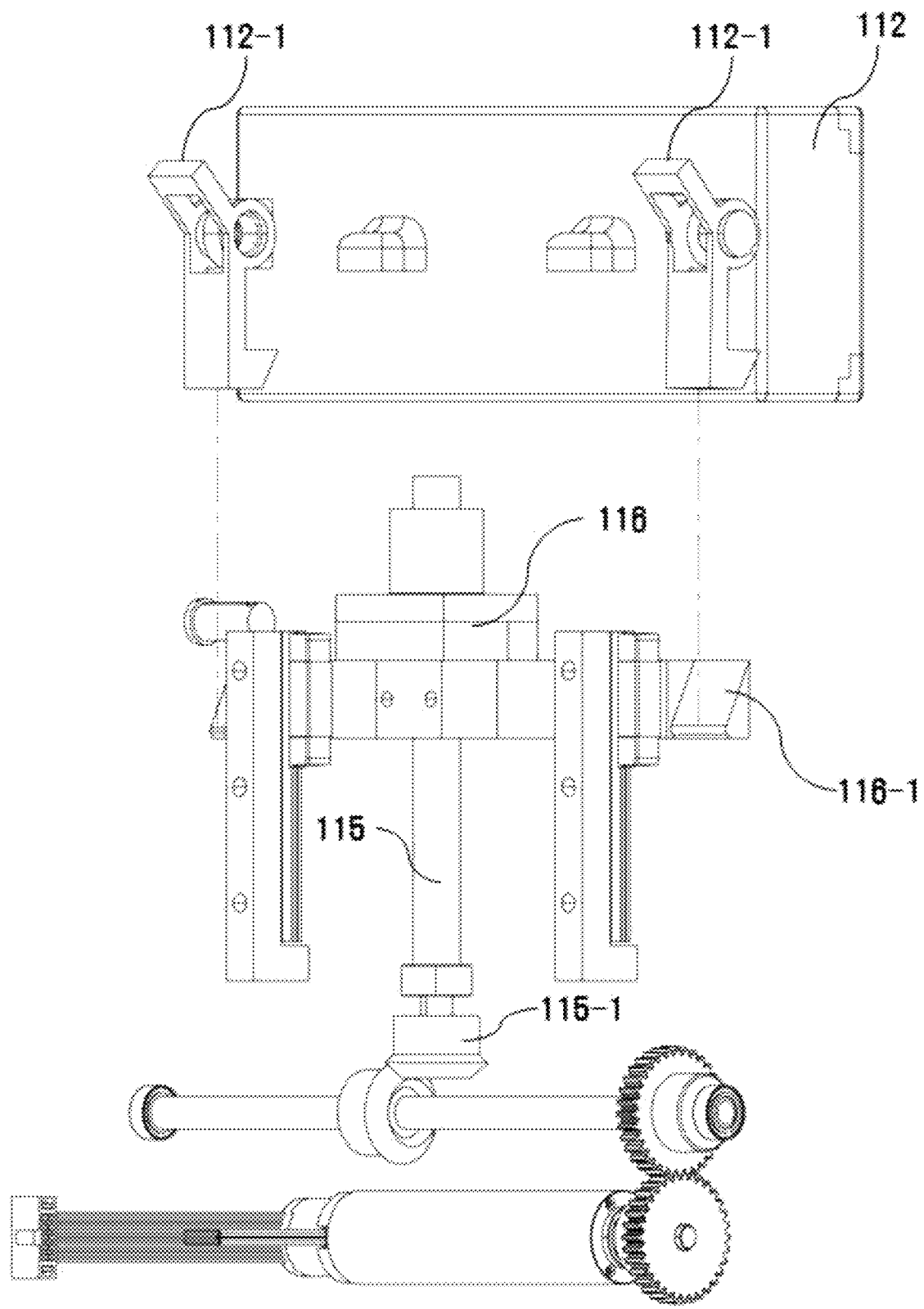
FIG. 13 is a perspective view showing that a roller unit of a first roller module of the inventive concept is separated in a cartridge form.

As a result, as shown in FIG. 13, the at least one roller 111 of the roller unit 110 may be mounted to and separated from the at least one shaft 114 of the roller unit 110 while sliding in the vertical direction (a replaceable cartridge type). In this case, a casing 112 of the roller unit 110 together with the at least one roller 111 of the roller unit 110 may be mounted to and separated from the at least one shaft 114. To this end, a first hook 112-1 of the casing 112 may be locked and unlocked. Further, the at least one roller 111 is rotatably coupled to the casing 112. The casing 112 may have at least one hole or groove defined therein corresponding to the at least one hole or groove 111-1 defined in the at least one roller 111. The hole or groove of the casing 112 may be defined in a bottom surface of the casing 112 and may extend upwards to a top of the casing 112. Due to this structure, the at least one roller 111 of the roller unit 110 may be mounted to and detached from the at least one shaft together with the casing while being accommodated in the casing 112 of the roller unit 110.

Further, in order to facilitate the mounting and detachment, the at least one hole or groove 111-1 of the at least one roller 111 of the roller unit 110 may extend in the vertical direction. Further, a horizontal cross-section of the at least one hole or groove 111-1 of the at least one roller 111 of the roller unit 110 and a horizontal cross-section of the at least one shaft 114 of the roller unit 110 may have a shape corresponding to each other.

In order to further secure the mounting and separation, each of a shape of the horizontal cross-section of the at least one hole or groove 111-1 of the at least one roller 111 of the roller unit 110 and a shape of the horizontal cross-section of the at least one shaft 114 of the roller unit 110 may have a shape extending in a first direction and a second direction in a horizontal plane and intersecting with each other at a center point in a right manner.

The roller unit 110 may rotate by the driving unit 120 in the rolling operation mode while the "vertical direction" axis is a rotation axis thereof.

Figure 10:
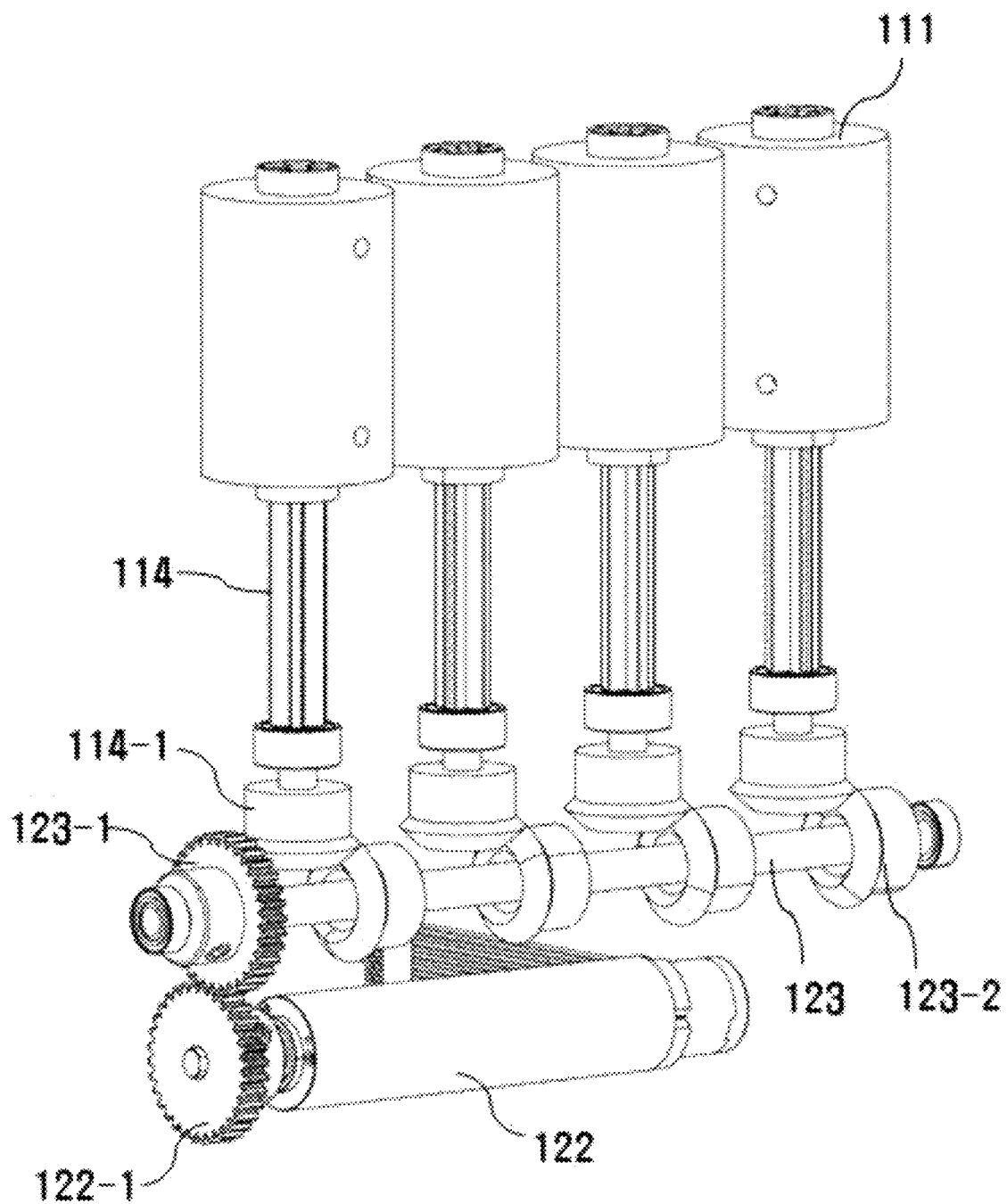
FIG. 10 is a perspective view showing a rolling operation mode of a first roller module of the inventive concept.

Referring to FIG. 10, for this purpose, the driving unit 120 may include a first driving motor 122. In one example, a rotation axis of the first driving motor 122 of the driving unit 120 and a rotation axis of the at least one shaft 114 of the roller unit 110 may be perpendicular to each other.

This may be implemented using a bevel gear. In this case, the driving unit 120 may further include a first driving shaft 123. A spur gear 122-1 of the first driving motor 122 of the driving unit 120 may mesh with a spur gear 123-1 of the first driving shaft 123 of the driving unit 120. At least one bevel gear 114-1 of the at least one shaft 114 of the roller unit 110 may mesh independently with at least one bevel gear 123-2 of the first driving shaft 123 of the driving unit 120.

That is, a driving force of the first driving motor 122 may be transmitted through the spur gear 122-1 of the first driving motor 122 and the spur gear 123-1 of the first driving shaft 123 to the first driving shaft 123. Furthermore, a driving force of the first driving shaft 123 may be transmitted through the at least one bevel gear 123-2 of the first driving shaft 123 and the bevel gear 114-1 of the at least one shaft 114 of the roller unit 110 to at least one shaft 114 of the roller unit 110.

The roller unit 110 of the first roller module 100 and the second roller unit 210 of the second roller module 200 may be moved by the base module 300 such that a spacing therebetween varies (clamping operation mode).

Figure 11A:
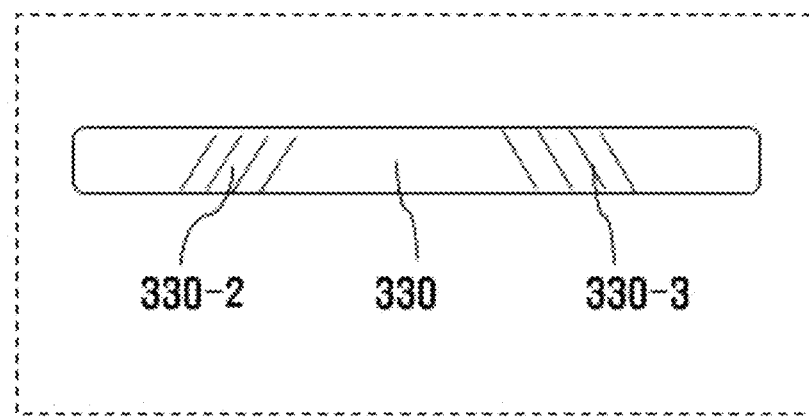
FIGS. 11A to 11C are perspective views showing a clamping operation mode of a first roller module and a second roller module of the inventive concept.
Figure 11B:
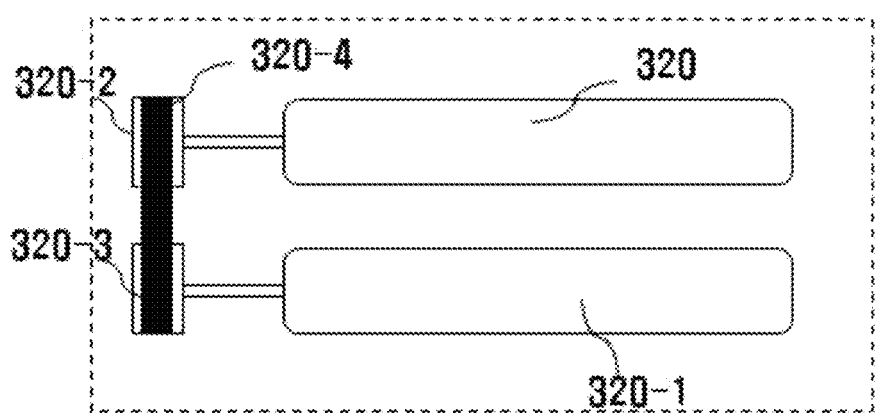
Figure 11C:
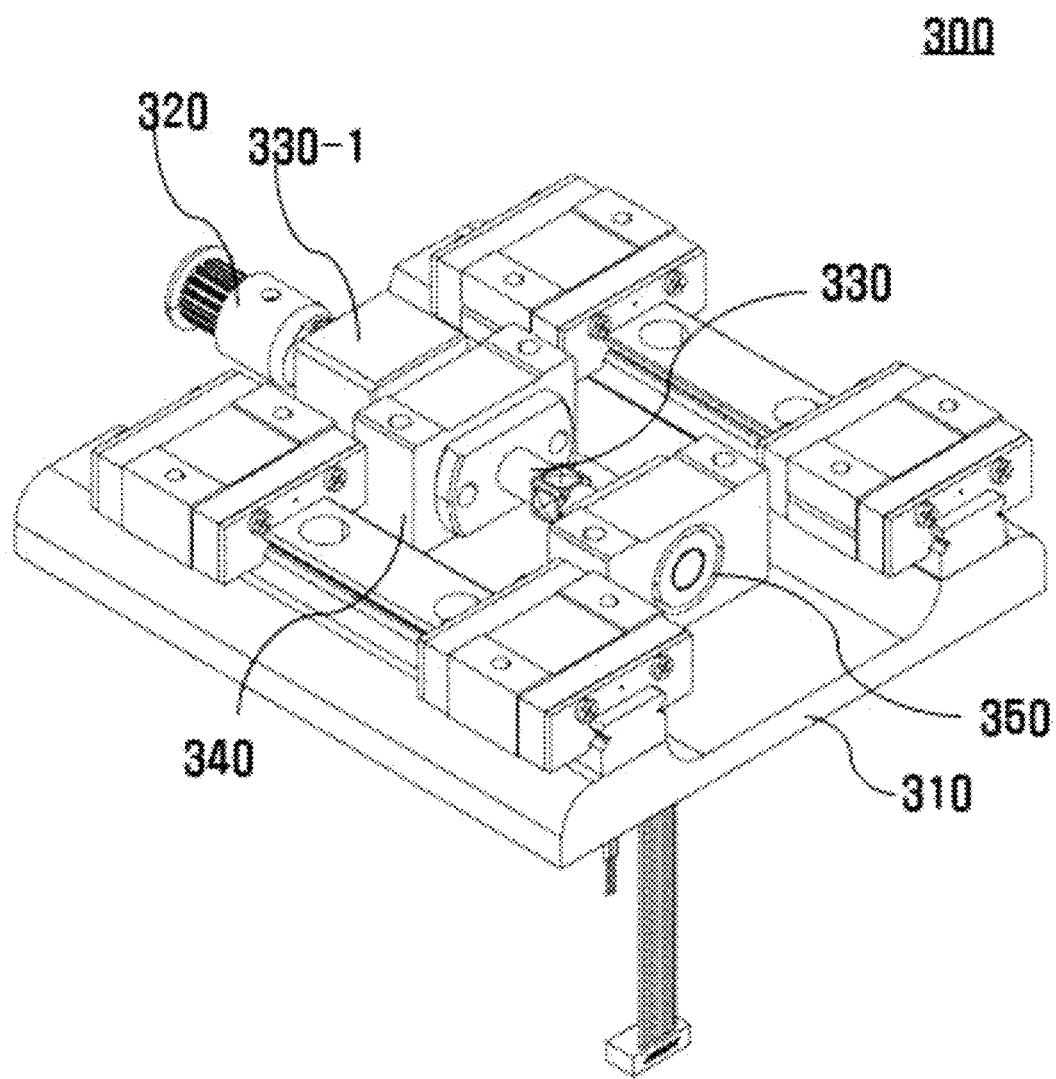

Referring to FIGS. 11A to 11C, for this purpose, the base module 300, may include a first base body 310, a first nut 340 disposed on the first base body 310 of the base module 300, and coupled to the first roller module 100, a second nut 350 disposed on the first base body 310 of the base module 300 and coupled to the second roller module 200, a screw 330 meshing with the first nut 340 of the base module 300 and the second nut 350 of the base module 300, and a first driving motor 320 to rotate the screw 330 of the base module 300.

In one example, a gearbox 330-1 may be disposed between the first driving motor 320 of the base module 300 and the screw 330 of the base module 300, so that a rotational speed and a torque of the screw 330 of the base module 300 may be adjusted.

In this case, the screw 330 of the base module 300 and the first nut 340 of the base module 300 and the second nut 350 of the base module 300 may operate in a "lead screw" or "ball screw" manner. That is, when the screw 330 of the base module 300 rotates, the first nut 340 of the base module 300 and the second nut 350 of the base module 300 may move along the screw 330 of the base module 300.

That is, a forward or reverse rotation of the screw 330 of the base module 300 may move the first nut 340 of the base module 300 and the second nut 350 of the base module 300 such that a spacing between the first roller module 100 and the second roller module 200 varies.

To this end, a spiral rotation direction 330-2 in which the screw 330 of the base module 300 and the first nut 340 of the base module 300 mesh with each other, and a spiral rotation direction 330-3 in which the screw 330 of the base module 300 and the second nut 350 of the base module 300 mesh with each other may be opposite to each other (see FIG. 11A).

In one example, in order to precisely control the rotation of the first driving motor 320, the base module 300 may further include a second driving motor 320-1, and a belt 320-4 connecting a spur gear 320-2 of the first driving motor 320 of the base module 300 and a spur gear 320-3 of the second driving motor 320-1 of the base module 300 to each other. The rotation of the first driving motor 320 of the base module 300 and the rotation of the second driving motor 320-1 of the base module 300 may be associated with each other via the belt 320-4 of the base module 300 (see FIG. 11B).

The roller unit 110 may move in the "vertical direction" by the driving unit 120 (vertical operation mode).

Figure 12:
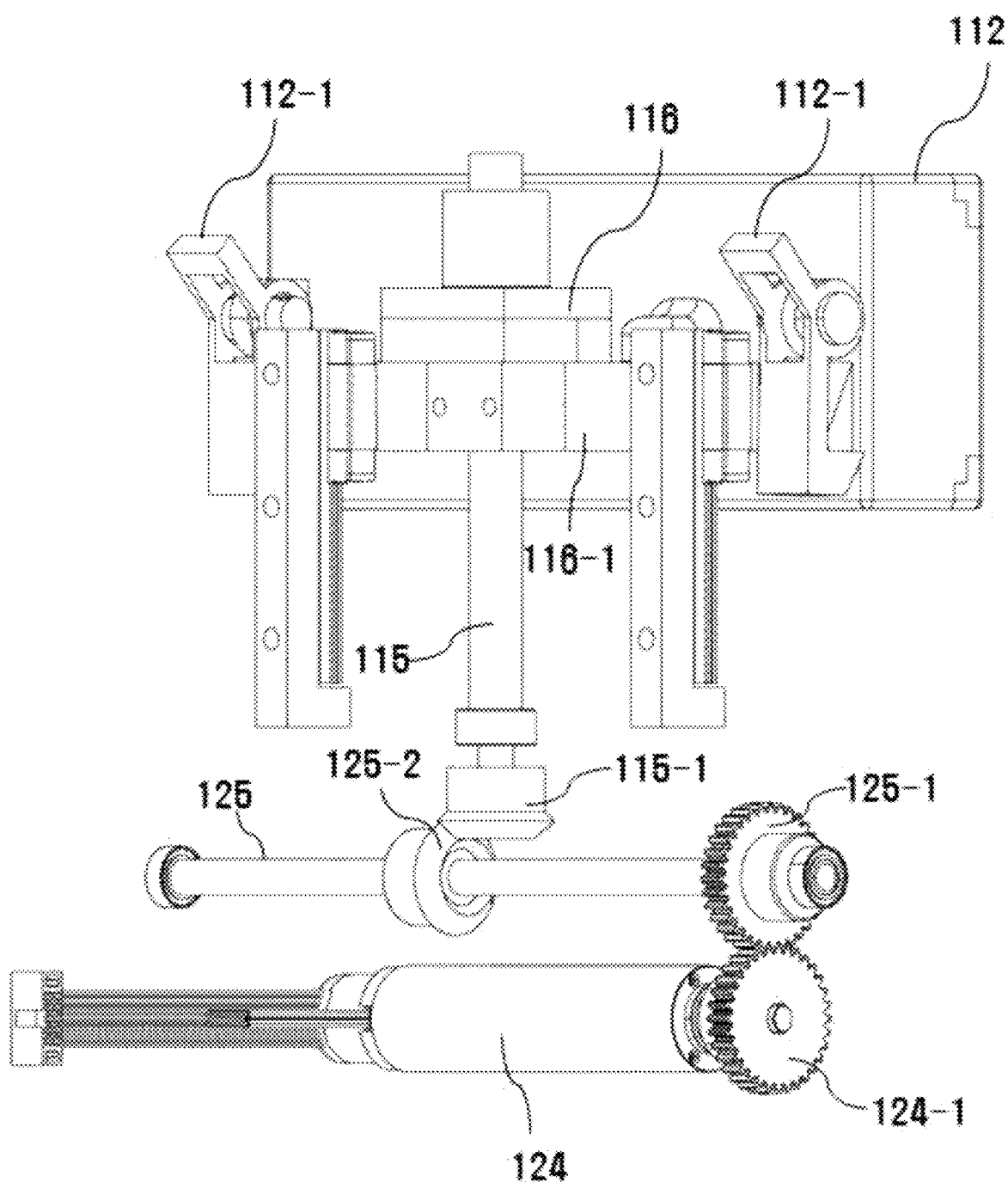
FIG. 12 is a perspective view showing a vertical operation mode of a first roller module of the inventive concept.

Referring to FIG. 12, for this purpose, the roller unit 110 may further include a screw 115, a nut 116 meshing with the screw 115 of the roller unit 110, and the casing 112 disposed on the nut 116 of the roller unit 110.

In this case, the screw 115 of the roller unit 110 may be rotated by the driving unit 120, and the nut 116 of the roller unit 110 may be moved in the vertical direction by the rotation of the screw 115 of the roller unit 110.

That is, the screw 115 of the roller unit 110 and the nut 116 of the roller unit 110 may operate in the "lead screw" or "ball screw" manner. That is, the rotation of the screw 115 of the roller unit 110 may allow the nut 116 of the roller unit 110 to move along the screw 115 of the roller unit 110.

In this case, the casing 112 of the roller unit 110 may be moved vertically by the nut 116 of the roller unit 110. Furthermore, the at least one roller 111 of the roller unit 110 may move in a vertical direction together with the casing 112 of the roller unit 110.

In one example, in order to stably support the casing 112 of the roller unit 110 while moving in the vertical direction, the casing 112 of the roller unit 110 may include a pivoting hook 112-1. The nut 116 of the roller unit 110 may include a bar 116-1 that is locked and unlocked by the hook 112-1 of the casing 112 (see FIG. 13).

In this case, the number of the hooks 112-1 of the casing 112 of the roller unit 110 may be two which may be disposed at both ends of the bar 116-1 of the nut 116, respectively.

In one example, in order to transmit the driving force to the screw 115 of the roller unit 110, the driving unit 120 may include a second driving motor 124. The rotation axis of the second driving motor 124 of the driving unit 120 and the rotation axis of the screw 115 of the roller unit 110 may be perpendicular to each other.

This may be implemented using a bevel gear. In this connection, the driving unit 120 may further include a second driving shaft 125. A spur gear 124-1 of the second driving motor 124 of the driving unit 120 may mesh with a spur gear 125-1 of the second driving shaft 125 of the driving unit 120. A bevel gear 115-1 of the screw 115 of the roller unit 110 may mesh with a bevel gear 125-2 of the second driving shaft 125 of the driving unit 120.

That is, the driving force of the second driving motor 124 may be transmitted through the spur gear 124-1 of the second driving motor 124 and the spur gear 125-1 of the second driving shaft 125 to the second driving shaft 125. Furthermore, the driving force of the second driving shaft 125 may be transmitted through the bevel gear 125-2 of the second driving shaft 125 and the bevel gear 115-1 of the screw 115 of the roller unit 110 to the screw 115 of the roller unit 110.

In one example, the driving unit 120 may include a box-shaped housing 121. The first driving motor 122, the first driving shaft 123, the second driving motor 124, and the second driving shaft 125 may be disposed inside the housing 121 of the driving unit 120.

Further, a lower portion of the at least one shaft 114 of the roller unit 110 may be disposed inside the housing 121 of the driving unit 120.

Further, the housing 121 of the driving unit 120 is supported by the first nut 340 of the base module 300. Thus, in the clamping operation mode, the driving unit 120 and the roller unit 110 may be guided and moved by the first nut 340.

In the medical robot of the inventive concept, the surgical tool (the balloon catheter) may be transferred using the roller module, and the roller of the roller unit may be manufactured in a form of a replaceable cartridge. Therefore, after one time surgery, a contaminated roller cartridge may be replaced with a new roller cartridge. The medical robot of the inventive concept may be used more hygienically than the general robot unit may be.

Further, in the medical robot of the inventive concept, the clamping degree of the surgical tool may be controlled by adjusting a distance between the first roller module and the second roller module facing away each other, thereby to precisely control a travel direction of the surgical tool. Further, the travel direction of the surgical tool may be precisely controlled via the vertical operation mode of the first roller module and the second roller module facing away each other.

Further, the inventive concept provides the driving device for the medical robot constituting the medical robot, and the roller module for the medical robot constituting the driving device for the medical robot.

The effects of the inventive concept are not limited to the effects mentioned above. Other effects not mentioned will be clearly understood by those skilled in the art from the following description.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A driving device for a medical robot, the driving device comprising:
   a base module; and
   a first roller module and a second roller module, wherein a spacing between the first roller module and the second roller module is controlled by the base module,
   wherein at least one of the first roller module or the second roller module includes:
   a driving unit; and
   a roller unit rotated by the driving unit while a rotation axis of the roller unit is a vertical direction,
   wherein the roller unit includes at least one roller, and at least one shaft independently coupled to the at least one roller of the roller unit and rotated by the driving unit,
   wherein the at least one roller of the roller unit has at least one hole or groove defined therein in which at least a portion of the at least one shaft of the roller unit is independently received, and
   wherein at least one of the roller unit of the first roller module and the roller unit of the second roller module is configured to move in the vertical direction by the driving unit to rotate a surgical tool clamped between the roller unit of the first roller module and the roller unit of the second roller module.

2. The driving device of claim 1, wherein at least one of a guide catheter, a guide wire, and a balloon catheter is disposed and clamped between the first roller module and the second roller module, and then is transferred via rotation of the roller unit of the first roller module and the roller unit of the second roller module, and
   wherein rotation axes of the roller unit of the first roller module and the roller unit of the second roller module are parallel to each other, and rotation directions of the roller unit of the first roller module and the roller unit of the second roller module are opposite to each other.

3. The driving device of claim 1, wherein each of the roller unit of the first roller module and the roller unit of the second roller module is removable in a cartridge form.

4. The driving device of claim 1, wherein the base module includes:
   a base body;
   a first nut disposed on the base body of the base module and coupled to the first roller module;
   a second nut disposed on the base body of the base module and coupled to the second roller module;
   a screw meshing with the first nut of the base module and the second nut of the base module; and
   a first driving motor to rotate the screw of the base module,
   wherein forward or reverse rotation of the screw of the base module allows the first nut of the base module and the second nut of the base module to move such that a spacing between the first roller module and the second roller module varies.

5. The driving device of claim 4, wherein a gearbox is disposed between the first driving motor of the base module and the screw of the base module.

6. The driving device of claim 4, wherein the base module further includes a second driving motor, and a belt connecting a spur gear of the first driving motor of the base module and a spur gear of the second driving motor of the base module to each other, and wherein rotation of the first driving motor of the base module and rotation of the second driving motor of the base module are associated with each other via the belt of the base module.

7. The driving device of claim 4, wherein a spiral rotation direction in which the screw of the base module and the first nut of the base module mesh with each other, and a spiral rotation direction in which the screw of the base module and the second nut of the base module mesh with each other are opposite to each other.

8. A medical robot comprising:
a first driving device, a second driving device, and a third driving device to transport a guide catheter, a guide wire, and a balloon catheter, respectively,
wherein at least one of the first driving device, the second driving device, or the third driving device includes:
a base module; and
a first roller module and a second roller module, wherein a spacing between the first roller module and the second roller module is controlled by the base module,
wherein at least one of the first roller module or the second roller module includes:
a driving unit; and
a roller unit rotated by the driving unit while a rotation axis of the roller unit is a vertical direction,
wherein the roller unit includes at least one roller, and at least one shaft independently coupled to the at least one roller of the roller unit and rotated by the driving unit,
wherein the at least one roller of the roller unit has at least one hole or groove defined therein in which at least a portion of the at least one shaft of the roller unit is independently received,
wherein at least one of the guide catheter, the guide wire, and the balloon catheter is disposed and clamped between the first roller module and the second roller module, and then is transferred via rotation of the roller unit of the first roller module and the roller unit of the second roller module,
wherein rotation axes of the roller unit of the first roller module and the roller unit of the second roller module are parallel to each other, and rotation directions of the roller unit of the first roller module and the roller unit of the second roller module are opposite to each other, and
wherein at least one of the roller unit of the first roller module and the roller unit of the second roller module is configured to move in the vertical direction by the driving unit to rotate a surgical tool clamped between the roller unit of the first roller module and the roller unit of the second roller module.

9. The medical robot of claim 8, wherein the guide catheter is clamped to the first driving device, the guide wire is clamped to the second driving device, the balloon catheter is clamped to the third driving device, and
wherein the guide catheter accommodates the guide wire and the balloon catheter therein.

10. The medical robot of claim 8, wherein a travel direction of the first driving device and a travel direction of the second driving device are in the same straight line, while the travel direction of the first driving device and a travel direction of the third driving device intersect with each other.

\* \* \* \* \*